United States Patent
Sjoboen

[19]

[11] Patent Number: 6,102,249
[45] Date of Patent: Aug. 15, 2000

[54] JAM RESISTANT DISPENSER FOR CAPILLARY TUBES AND THE LIKE

[75] Inventor: Lauren R. Sjoboen, Austin, Tex.

[73] Assignee: University of Washington, Seattle, Wash.

[21] Appl. No.: 09/026,931

[22] Filed: Feb. 20, 1998

Related U.S. Application Data

[60] Provisional application No. 60/039,023, Feb. 21, 1997.

[51] Int. Cl.⁷ .................................................. B65G 59/00
[52] U.S. Cl. .......................................... 221/256; 221/268
[58] Field of Search ..................................... 221/155, 255, 221/256, 281, 268, 276, 271, 263, 264, 266, 312 R

[56] References Cited

U.S. PATENT DOCUMENTS

| | | | |
|---|---|---|---|
| 1,517,952 | 12/1924 | Capparella | 221/266 |
| 4,960,566 | 10/1990 | Mochida | 422/65 |
| 5,363,984 | 11/1994 | Laind, III | 221/266 |

FOREIGN PATENT DOCUMENTS

| | | | |
|---|---|---|---|
| 941384 | 7/1948 | France | 221/256 |

*Primary Examiner*—Kenneth W. Noland
*Attorney, Agent, or Firm*—Delbert J. Barnard

[57] ABSTRACT

A jam resistant dispenser (10) including a storage housing (14) of a size and shape to store and dispense a plurality of substantially identical cylindrical members (12), preferably, capillary tubes for gene sequencing reactions and other chemical/biological processes. Housing (14) includes a base (22), an interior (24) defined by a front wall (16), back wall (18), two end walls (20) and the base (22). Base (22) includes an open throat (32) of a size to receive at least seven cylindrical members (12) laid out side by side and parallel to base (22) in order to prevent a naturally occurring arch or bridge of the cylindrical members from forming. Dispenser (10) also includes a sliding tray (46) having an exit slot (48) of a size to completely receive and support one cylindrical member (12). During sliding movement, the exit slot (48) is positionable along any portion of the open throat in order to receive one cylindrical member from the throat. Once the exit slot is filled with the one cylindrical member, the sliding tray is slid laterally to a position where at the extracted cylindrical member is removed from the tray while the tray confronts the base and the open throat so other cylindrical members are not released.

14 Claims, 2 Drawing Sheets

US 6,102,249

JAM RESISTANT DISPENSER FOR CAPILLARY TUBES AND THE LIKE

RELATED APPLICATIONS

This application claims priority to provisional application Ser. No. 60/039,023 filed Feb. 21, 1997.

STATEMENT OF INTEREST

This application is based upon research funded in cooperation with NIH grant No. 1 RO1 HG01497-01. As such, the United States Government may have rights to this invention.

1. Technical Field

The present invention relates to a dispensing container for tubular or cylindrical members, such as capillary tubes and the like. More specifically, the present invention relates to a specific housing and sliding tray with an exit slot for dispensing a large volume of dispensing capillary tubes that is virtually jam resistant requiring no human intervention.

2. Background of the Invention

Automation in the preparation of biological samples for biomedical laboratories, and particularly the sequencing of human genetic code product, requires thousands of samples in an eight-hour period. Typically, the samples are contained and prepared inside glass capillaries instead of microplates in order to facilitate the handling of submicroliter fluid volumes, to minimize evaporation losses, and to speed up thermal cycling processes.

Preparation reactions inside glass capillaries requires that the capillaries be reliably and quickly inputted into an automated system, and that they remain uncontaminated. Existing dispensing systems such as vibration feeders, toothpick dispensers, and so on are inadequate as they cannot reliably dispense thousands of units in succession without jamming or without the need for human intervention.

Thus, it is an object of the present invention to provide a capillary tube dispenser that can provide thousands of output without jamming or without the need for human intervention.

DISCLOSURE OF THE INVENTION

The present invention relates to a jam-resistant dispenser that includes a storage housing of a size and shape to store and dispense a plurality of substantially identical cylindrical members, such as capillary tubes. The housing includes a front wall, a back wall, and a pair of oppositely-situated end walls that interconnect the front wall and the back wall. The housing also includes a base that joins the front wall, the back wall, and the two end walls to form an interior defined by the front wall, the back wall, the two end walls, and the base. The dispenser also includes an opening defined by an upper portion of the housing to receive the cylindrical members into the interior of the housing. The base also includes an open throat of a size to receive a plurality of cylindrical members that will naturally lay parallel to the base in a side by side arrangement within the throat and not inherently form and arch or a bridge.

The interior constrains each cylindrical member along each cylindrical member's length and its two ends such that each cylindrical member is aligned to gravitationally travel downwardly in the interior and ultimately into the open throat in order to exit the housing.

The dispenser also includes a sliding tray which includes an exit slot of a size to completely receive and support one cylindrical member. The sliding tray is positioned adjacent and confronting at least a portion of the base during lateral sliding movement of the tray. During sliding movement, the exit slot is positionable underneath any portion of the entire open throat in order to receive one cylindrical member from the housing through the throat.

According to one aspect of the present invention, the dispenser further includes at least one interior baffle positioned generally centrally of the interior in order to break up the perpendicular distance as measured from the throat into increments no greater than would allow the cylindrical member to rotate end on end. In preferred form, this increment is not greater than ½ the length of the cylindrical member. In this manner, the perpendicular, or vertical, distance that the tube must travel is of a length that does not allow the cylindrical member to rotate 180 degrees and cause a jam.

According to another aspect of the invention, the interior, defined by the end walls, includes a pair of oppositely-situated, concave-shaped interior walls. The concave shape allows for less breakage of fragile cylindrical members, such as capillary tubes, and puts the cylindrical members in its desired orientation at its lowest potential energy state. In preferred form, the concave-shaped interior walls also may include an inwardly directing baffle to complement the interior baffle such that the geometry of the serpentine path keeps the perpendicular distance as measured from the throat to ½ the length of the cylindrical member.

According to another aspect of the present invention, the interior walls further include two constricting oppositely-situated, concave-shaped interior bottom walls leading to and adjoining a pair of straight throat walls that adjoin the throat. The concave-shaped interior bottom walls further constrict and align the cylindrical members for ultimate exit through the throat. In another embodiment, the dispenser is naturally shaped to constrict the interior from the opening down to the throat. This constriction further aids the alignment such that the cylindrical members are less likely to jam during the natural gravitational travel of the cylindrical members from the opening to the throat.

In yet another embodiment of the present invention, the front wall may include a transparent portion in order to view the cylindrical members as they gravitationally travel to the throat.

These and other advantages, objects and features will become apparent from the following best mode description, the accompanying drawings, and the claims, which are all incorporated herein as part of the disclosure of the invention.

BRIEF DESCRIPTION OF THE DRAWINGS

Like reference numerals are used to designate like parts throughout the several views of the drawing, wherein.

BEST MODE FOR CARRYING OUT THE INVENTION

Figure 1:
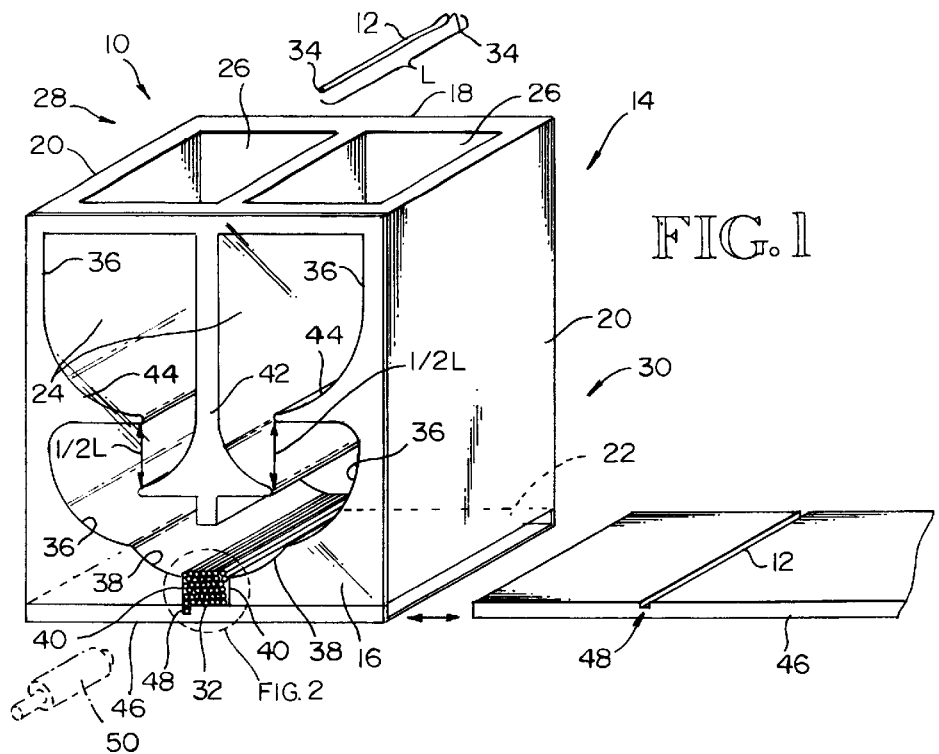
FIG. 1 is a pictorial view of the dispenser of the present invention having a storage housing defined by an interior having curved interior sidewalls and an interior baffle and with an outlet throat of a width to accommodate a multitude of capillary tubes; the dispenser also includes a sliding tray having an exit slot that is of a size to receive one capillary tube when slid underneath the throat; the extracted capillary tube may be accessed by an automatic gripper (shown in phantom) as part of an automated process.

Referring to FIG. 1, the present invention relates to a jam resistant dispenser 10 that can store and dispense a plurality of cylindrical members 12. Although the present invention can be used with cylindrical members such as straws, toothpicks and the like, the present invention was particularly designed for thousands of uniform capillary tubes used in continuous automated lab sequencing, such as for gene sequencing projects. The type of capillary tube used for this type of gene sequencing project is typically a 5 $\mu$L glass capillary (55 mm length and 838 $\mu$m outside diameter. These tubes are fragile and subject to bowing. Because the goal is to prepare a large number of samples in a relatively short period (i.e. 5,000 samples in an eight-hour period), it is imperative that the capillary tubes needed to process the samples are uniformly dispensed without the threat of capillary breakage or jamming that requires human intervention.

The dispenser 10 includes a storage bin, hopper, or housing 14. As shown, this housing is in the shape of a cube-like box having a front wall 16, a back wall 18, and a pair of oppositely-situated end walls 20 that interconnect the front wall to the back wall. Housing 14 also includes a base 22 that adjoins front wall 16 and back wall 18, and end walls 20 to form an interior 24 that is defined above base 22 and by and between front wall 16, back wall 18 and the two end walls 20.

Figure 2:
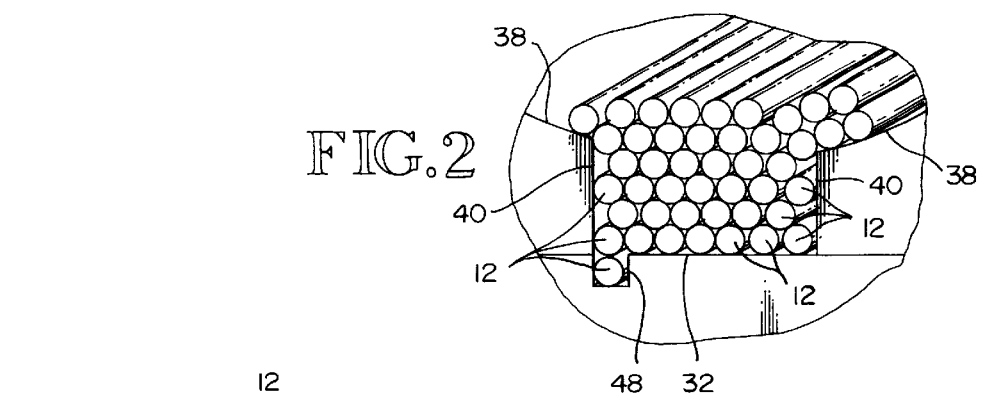
FIG. 2 is an enlarged detail of the exit slot and throat as shown in circle 2 of FIG. 1.

At the top end 26 of housing 14 is an opening 28 for easy loading of the large volume of capillary tubes 12. Located at the bottom end 30 of housing 14, is base 22 that includes an open throat 32. Referring also to FIG. 2, open throat 32 is of a size to receive enough capillary tubes (i.e. at least seven capillary tubes) to negate formation of an arch or bridge 12 and to be laid out side by side parallel to base 22. This advantage will be discussed further below.

The geometry of the interior is highly dependent upon the size and shape of the cylindrical members being dispensed. The interior 24 is of a size and shape to constrain the capillary tubes 12 such that the capillary tubes are supported along length L and ends 34 such that each capillary tube is parallelly aligned to throat 32. This constraint/support is necessary to prevent breakage and bowing. It is the throat that leads the capillary tubes to their ultimate exit from the dispenser.

It is preferred that interior 24 constricts from its open top 26 down to throat 32. In preferred form, the interior along end walls 20 are concave in shape to align the capillary tubes downwardly to the base and throat as well as to naturally constrict and concentrate the capillary tubes over the throat. In this manner, the curved walls provide that the orientation of the capillary tubes will be in the lowest potential energy state. In preferred form, the concave interior walls 36 also include further constricted concave bottom walls 38 that lead to and adjoin a pair of straight throat walls 40 that define throat 32.

Although not shown, one of the interior walls 36/bottom walls 38 combination may be slightly higher relative to the other bottom wall 38/interior wall 36 combination to provide a positive stop for the capillary tube as they descend downwardly along the slightly lower interior wall/bottom wall combination towards the slightly higher interior wall/ bottom wall combination. However, the concave shape of interior walls 36 and bottom walls 38 makes this feature relatively unnecessary as the capillary tube are already lined up by the nature of the curved walls.

As capillary tubes can become dislodged, flip around and thus jam the dispenser, the present invention also provides an interior baffle 42 that essentially divides the interior into two components. Thus, there are two separate, generally symmetrical, serpentine paths that the capillary tubes perpendicularly (vertically) travel to the throat 32. In combination with interior wall baffles 44, the vertical distance that the capillary tubes must traverse to reach the throat is no more than that which will allow the capillary tube to rotate end on end. In preferred form, this perpendicular distance is no greater than ½ the length (½ L) of the capillary tubes 12. In this manner, there is no room for the capillary tubes to make an 180 degree turn and jam the dispenser.

As shown in FIG. 1, interior baffle 42 is in combination with interior end wall baffles 44 and the curved (concave) walls to restrict the capillary tubes' range of position to that within which the curved walls can correct make correction possible.

For smaller volumes (i.e. less than 500), however, the interior baffle 42 is not required.

Figure 3:
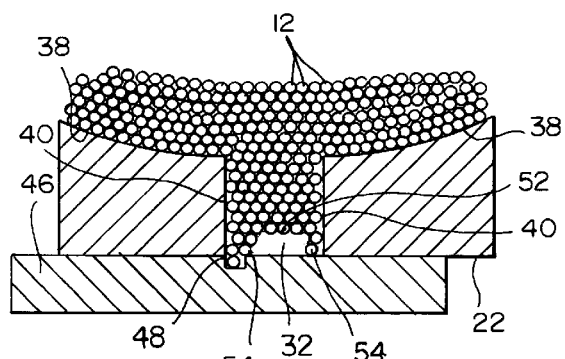
FIG. 3 is a sectional view of the capillary tubes inside the throat and showing the exit slot with its slidable tray relative to the base and throat of the housing to extract a single capillary tube.
Figure 4:
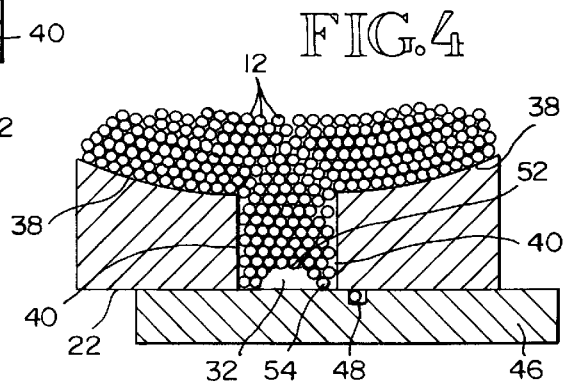
FIG. 4 is a view like FIG. 3 except showing the exit slot being slid along the base for removal of the capillary tube.

A key part of the invention is directed to a sliding tray 46 with an exit slot 48 that is of a size and shape to hold a single capillary tube 12. In preferred form, the exit slot is one capillary diameter deep and 33% larger than one capillary wide. The sliding tray 46 is of a size and shape to closely confront base 22 such that exit slot 48 can move underneath any portion of the entire open throat 32. This is best seen in FIGS. 3–4. As capillary tubes reach throat 32, exit slot 48 may be maneuvered either automatically or manually traverse the entire width of throat 32 to extract a single capillary tube 12 from throat 32. The sliding tray is moved under the base such that the single selected capillary tube 12 in exit slot 48 is supported from the top as well and would then be ready to be removed by an automated robotic gripper that would take the whole length of the capillary, shown in phantom at 50, to reduce bowing. Alternatively, the capillary tube may be removed manually.

The sliding tray can be manually operated (as shown), but if the dispenser is used in an automated process, the sliding movement can be obtained through a rotating cylinder or continuous belt (not shown).

Figure 5:
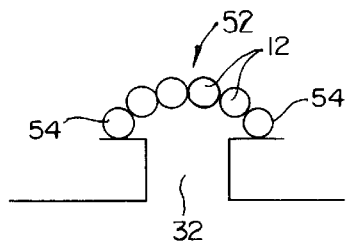
FIG. 5 is a schematic view showing an undesirable arch or bridge of capillaries over a too narrow throat.

Referring now to FIGS. 2–5, it has been found in testing that less than seven capillary tubes (typically four to five) will tend to arc as shown in FIGS. 3–5. This arching or bridging leads to jamming and potential breakage of the capillary tubes. Thus, throat 32 is of a width to hold at least seven capillary tubes side by side. However, as seen in FIGS. 3 and 4, small arches 52 can still occur. As such, the exit slot incorporated into the sliding tray is particularly effective for relieving these jams. As shown in FIGS. 3–5, the arched capillary tubes form two pillars 54, one at each end of the arch. As shown in FIGS. 3–4, once the exit slot passes through the open throat, and directly underneath one of the support pillars 54 of the arch 52, one of the support capillaries is removed, thus avoiding a misfeed problem.

Figure 6:
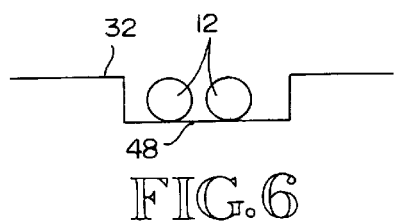
FIG. 6 and FIG. 7 are examples of an undesirably wide exit slot.
Figure 7:
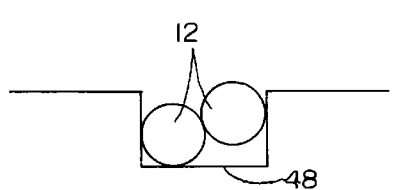
Figure 8:
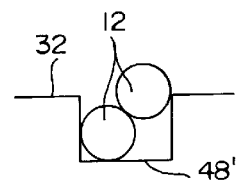
FIGS. 8 and 9 are schematic views showing alternate acceptable exit slots.
Figure 9:
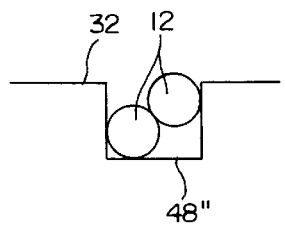

Although the exit slot is designed only to contain one capillary tube, alternate embodiments of the exit slot 48 are shown in FIGS. 8 and 9 as examples of acceptable alternatives (and marked 48' and 48"). The schematic views of FIGS. 6 and 7 show undesirable exit slot widths, as the excess width tends to jam the exit slot and the throat.

Fiber optic reflective sensors (not shown) may also be used for positive determination of all motions and to sense if a capillary tube has actually dropped into the exit slot. After approximately 50 capillary tube dispensing sequences, the sliding tray/exit slot may need to traverse the throat more than once (i.e. twice) to pick up a new capillary tube.

Figure 10:
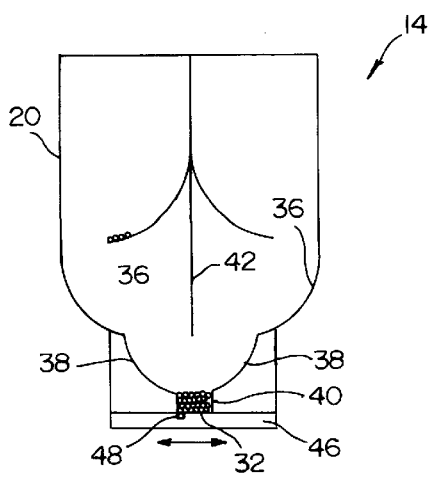
FIG. 10 is a schematic view of an alternate embodiment of the interior baffle arrangement.
Figure 11:
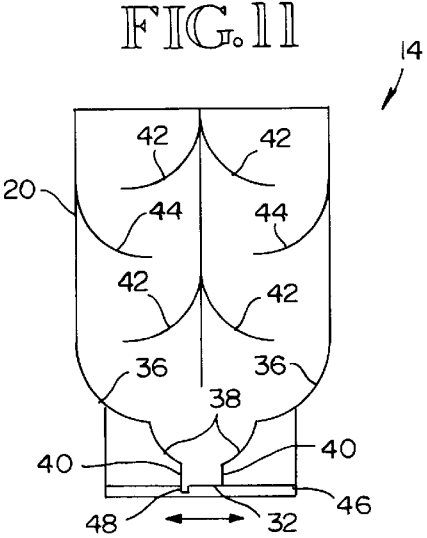
FIG. 11 is a schematic view of an alternate embodiment of an extended baffle arrangement to accommodate a larger volume of capillary tubes.

The present invention is designed to hold 2500–5000 capillary tubes. Additional baffles may be added to hold a higher number of capillary tubes, for example, 10,000. An additional baffle arrangement is shown schematically in FIG. 11. Alternate baffle arrangements can also be used, such as shown schematically in FIG. 10 for the 2500–5000 range.

The preferred invention can be made out of metal (e.g. aluminum) or man-made material. The front wall may include a transparent portion so that the capillary tubes may be visibly viewed by the researcher/technician. The materials that are selected need to be strong and lightweight, but also able to withstand sterilization without damage, depending upon the allowable contamination level for the sampling and testing. In the form shown in FIG. 1, the entire dispenser loaded with capillary tubes, may be sterilized.

The illustrated embodiments are only examples of the present invention and, therefore, are non-limitive. It is to be understood that many changes in the particular structure, materials and features of the invention may be made without departing from the spirit and scope of the invention. Therefore, it is the applicant's intention that its patent rights not be limited by the particular embodiments illustrated and described herein, but rather determined by the following claims, interpreted according to accepted doctrines of claim interpretation, including use of the doctrines of equivalents and reversal of parts.

What is claimed is:

1. A jam resistant dispenser comprising:
    a storage housing of a size and shape to store a plurality of substantially identical cylindrical members, said housing including a front wall, a back wall, and a pair of oppositely situated end walls that interconnect the front wall and the back wall, said housing also including a base that joins the front wall, the back wall, and the two end walls, thus forming an interior defined by the front wall, the back wall, the two end walls, and the base;
    an opening in said housing to receive the cylindrical members into the interior of said housing;
    said base including an open throat that extends downwardly from an opening in the base, said throat and opening being of a size narrower than said base, said throat being sized to receive a plurality of cylindrical members that will naturally lay parallel in a side by side arrangement in the open throat and will not inherently form an arch or bridge;
    said interior constraining each said cylindrical member along each cylindrical member's length and its two ends such that each cylindrical member is aligned to gravitationally travel parallel to said base into the open throat in order to exit the housing; and
    a sliding tray below said base including an exit slot of a size to completely receive and support one cylindrical member, said sliding tray being adjacent and confronting at least a portion of said base during lateral sliding movement of said tray, wherein during lateral sliding movement said exit slot is positionable underneath any portion of the open throat in order to receive one cylindrical member from the housing through the throat.

2. The dispenser according to claim 1, further comprising at least one interior baffle positioned generally centrally of the interior to break up the perpendicular distance from the throat into increments no greater than would allow the cylindrical member to rotate end on end.

3. The dispenser according to claim 1, wherein the front wall includes a transparent portion to view the cylindrical members.

4. The dispenser according to claim 1, wherein the number of cylindrical members laying parallel in a side by side arrangement is at least seven.

5. A jam resistant dispenser comprising:
    a storage housing of a size and shape to store and dispense a plurality of substantially identical cylindrical members, said housing including a front wall, a back wall, and a pair of oppositely situated end walls that interconnect the front wall and the back wall, said housing also including a base that joins the front wall, the back wall, and the two end walls, thus forming an interior defined by the front wall, the back wall, the two end walls, and the base;
    an opening defined by an upper portion of said housing to receive the cylindrical members into the interior of said housing;
    said base including an open throat of a size to receive a plurality of cylindrical members that will naturally lay parallel in a side by side arrangement and not inherently form an arch or bridge;
    said interior constraining each said cylindrical member along each cylindrical member's length and its two ends such that each cylindrical member is aligned to gravitationally travel parallel to said base into the open throat in order to exit the housing; and
    a sliding tray including an exit slot of a size to completely receive and support one cylindrical member, said sliding tray being adjacent and confronting at least a portion of said base during lateral sliding movement of said tray, wherein during lateral sliding movement said exit slot is positionable underneath any portion of the open throat in order to receive one cylindrical member from the housing through the throat; and
    wherein the interior, defined by the end walls, includes a pair of oppositely-situated concave-shaped interior walls.

6. The dispenser according to claim 5, further comprising at least one inwardly directed baffle from each interior wall.

7. The dispenser according to claim 6, further comprising at least one interior baffle positioned generally centrally of the interior to break up the perpendicular distance from the throat into increments no greater than would allow the cylindrical member to rotate end on end.

8. The dispenser according to claim 5, wherein the interior walls further include two constricting oppositely-situated, concave-shaped interior bottom walls leading to and adjoining a pair of straight throat walls that adjoin the throat.

9. The dispenser according to claim 8, wherein the interior is constricted from the opening downwardly to the open throat, such that the cross sectional area of the opening is larger than that of the throat.

10. A jam resistant dispenser comprising:

a storage housing of a size and shape to store and dispense a plurality of substantially identical cylindrical members, said housing including a front wall, a back wall, and a pair of oppositely situated end walls that interconnect the front wall and the back wall, said housing also including a base that joins the front wall, the back wall, and the two end walls, thus forming an interior defined by the front wall, the back wall, the two end walls, and the base;

an opening defined by an upper portion of said housing to receive the cylindrical members into the interior of said housing;

said base including an open throat of a size to receive a plurality of cylindrical members that will naturally lay parallel in a side by side arrangement and not inherently form an arch or bridge;

said interior constraining each said cylindrical member along each cylindrical member's length and its two ends such that each cylindrical member is aligned to gravitationally travel parallel to said base into the open throat in order to exit the housing; and a sliding tray including an exit slot of a size to completely receive and support one cylindrical member, said sliding tray being adjacent and confronting at least a portion of said base during lateral sliding movement of said tray, wherein during lateral sliding movement said exit slot is positionable underneath any portion of the open throat in order to receive one cylindrical member from the housing through the throat; and wherein the interior, defined by the end walls, includes a pair of oppositely-situated concave-shaped interior walls.

11. The dispenser according to claim 10, wherein the interior walls further include two constricting oppositely-situated, concave-shaped interior bottom walls leading to and adjoining a pair of straight throat walls that adjoin the throat.

12. The dispenser according to claim 11, wherein the front wall includes a transparent portion to view the cylindrical members.

13. A jam resistant dispenser comprising:

a storage housing of a size and shape to store and dispense a plurality of substantially identical cylindrical members, said housing including a front wall, a back wall, and a pair of oppositely situated end walls that interconnect the front wall and the back wall, said housing also including a base that joins the front wall, the back wall, and the two end walls, thus forming an interior defined by the front wall, the back wall, the two end walls, and the base;

an opening defined by an upper portion of said housing to receive the cylindrical members into the interior of said housing;

said base including an open throat of a size to receive a plurality of cylindrical members that will naturally lay parallel in a side by side arrangement and not inherently form an arch or bridge;

said interior constraining each said cylindrical member along each cylindrical member's length and its two ends such that each cylindrical member is aligned to gravitationally travel parallel to said base into the open throat in order to exit the housing; and a sliding tray including an exit slot of a size to completely receive and support one cylindrical member, said sliding tray being adjacent and confronting at least a portion of said base during lateral sliding movement of said tray, wherein during lateral sliding movement said exit slot is positionable underneath any portion of the open throat in order to receive one cylindrical member from the housing through the throat; and wherein the interior is constricted from the opening downwardly to the open throat, such that the cross sectional area of the opening is larger than that of the throat.

14. A jam resistant dispenser comprising:

a storage housing of a size and shape to store and dispense a plurality of substantially identical cylindrical members, said housing including a front wall, a back wall, and a pair of oppositely situated end walls that interconnect the front wall and the back wall, said housing also including a base that joins the front wall, the back wall, and the two end walls, thus forming an interior defined by the front wall, the back wall, the two end walls, and the base;

an opening defined by an upper portion of said housing to receive the cylindrical members into the interior of said housing;

said base including an open throat of a size to receive a plurality of cylindrical members that will naturally lay parallel in a side by side arrangement and not inherently form an arch or bridge;

said interior constraining each said cylindrical member along each cylindrical member's length and its two ends such that each cylindrical member is aligned to gravitationally travel parallel to said base into the open throat in order to exit the housing; and a sliding tray including an exit slot of a size to completely receive and support one cylindrical member, said sliding tray being adjacent and confronting at least a portion of said base during lateral sliding movement of said tray wherein during lateral sliding movement said exit slot is positionable underneath any portion of the open throat in order to receive one cylindrical member from the housing through the throat; and wherein the interior is constricted from the opening downwardly to the open throat, such that the cross sectional area of the opening is larger than that of the throat.

* * * * *